United States Patent [19]

Mazarguil et al.

[11] 3,941,657

[45] Mar. 2, 1976

[54] PURIFICATION OF D-AMINOACID OXIDASE

[75] Inventors: Honoré Mazarguil, Ramonville-St. Agne; François Meiller, Palaiseau; Pierre Monsan, Toulouse, all of France

[73] Assignee: Rhone-Poulenc Industries, Courbevoie, France

[22] Filed: Apr. 16, 1975

[21] Appl. No.: 568,797

[30] Foreign Application Priority Data
Apr. 22, 1974 France.............................. 74.13865

[52] U.S. Cl............ 195/66 R; 195/68; 195/DIG. 11
[51] Int. Cl.$^2$............................................ C07G 7/02
[58] Field of Search........ 195/66 R, 63, 68, DIG. 11

[56] References Cited
UNITED STATES PATENTS 3,652,761  3/1972  Weetall........................ 195/DIG. 11
3,746,622  7/1973  Nishikawa et al................. 195/66 R

*Primary Examiner*—Lionel M. Shapiro
*Attorney, Agent, or Firm*—McDougall, Hersh & Scott

[57] ABSTRACT

Process for the separation and purification of d-aminoacid oxidase by affinity chromatography. The process comprises contacting a mixture of proteins containing the d-aminoacid oxidase with a mineral carrier carrying haloalkylsilane grafts, upon which are fixed — NH — $(CH_2)_3$ — NH — $(CH_2)_2$ $C_6H_4$ COOH residues. The enzyme retained by the carrier is then separated by a solution of ethyleneglycol. Use of the pure d-aminoacid oxidase for the preparation of cetonic acids.

4 Claims, No Drawings

PURIFICATION OF D-AMINOACID OXIDASE

The present invention concerns a process for the separation and purification of d-aminoacid oxidase by affinity chromatography.

Affinity chromatography is a known method of separation and purification, which is applied in particular to enzymes. In this case, it comprises fixing, by means of covalent bonds, either the enzymes or the impurities, on carriers represented by organic gels, such as modified dextrane or polyacrylamide, then, when it is the enzyme that is fixed, detaching the enzyme from the carrier, by modifying the elution conditions of the medium.

However, the gels used suffer from a number of disadvantages. They are unstable and have little resistance to heat, pressure and microorganisms. This reduces their time of use, and their efficiency.

The process of the invention overcomes these disadvantages as the carriers used are stable and resistant to heat, pressure and microorganisms, and make it possible to separate, without difficulty, d-aminoacid oxidase from mixtures thereof with other inactive proteins, and to produce same in a high state of purity.

The process comprises contacting a solution of the mixture of proteins, containing the d-aminoacid oxidase, with a carrier onto which the enzyme is fixed, then separating the d-aminoacid oxidase from the carrier, and is characterized in that the carrier is a mineral carrier bearing haloalkylsilane grafts, upon which are fixed residues having the formula $-NH-(CH_2)_3-NH-(CH_2)_2C_6H_4$ COOH, and separating the purified d-aminoacid oxidase from the carrier by a solution of the ethyleneglycol.

The grafted carrier comprises oxides, hydroxides or other porous, insoluble mineral compounds on which are grafted, substituted or unsubstituted, haloalkylsilane groups whose alkyl residue comprises from 3 to 11 carbon atoms. These carriers and the process for the preparation thereof are described in French patent application No. 74.13687, Ser. No. 568,797 filed Apr. 19, 1974, correspondng to United States patent application filed concurrently herewith, by the same applicants, and entitled "Grafted Mineral Carriers for Fixing Enzymes".

In order to carry out the process of the present invention, it is essential that the carrier have a good capacity for fixing the d-aminoacid oxidase in order for it to be retained on the carrier during the separation operation, but without this fixing being too stable, in order to permit the d-aminoacid oxidase to be separated from the carrier.

Mineral carriers, grafted with haloalkylsilane groups, give stable complexes with the enzyme. It is therefore necessary to modify the carrier to be used.

The carrier is modified by replacing the halogen of the graft by a residue having the formula:

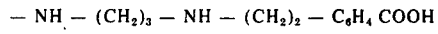

The process for modifying the graft comprises:
a. reacting the grafted carrier with the compound having the formula: $H_2N - (CH_2)_3 - NH - (CH_2)_2 - C_6H_4$ COOC$_2$H$_5$ in accordance with any known processes, and in particular in suspension at boiling temperature; then b. converting the ester function into an acid function by the action of any concentrated acid, in particular hydrochloric acid.

When purifying the d-aminoacid oxidase, a column for chromatography is filled with the modified carrier, balanced at the pH-value which is compatible with the enzyme, then the mixture of proteins containing the d-aminoacid oxidase in buffer solution is circulated in the column. The carrier is then washed with water to remove the absorbed inactive proteins.

The d-aminoacid oxidase is then separated from the carrier by dissolution in a solution of ethyleneglycol in a concentration of less than 50% by volume.

The d-aminoacid oxidase produced is pure and virtually all of the activity of the initial mixture is to be found again in the purified enzyme.

The d-aminoacid oxidase, which has been purified in this way, is particularly suitable for the production of cetonic acids such as pyruvic acid.

An embodiment of the invention is given hereinafter by way of illustration, but without limitation.

Preparation of the grafted carrier:

An aqueous solution of sodium silicate, corresponding to 220 g/l of SiO$_2$, is added dropwise to 230 ml of a 120 g/l aqueous solution of H$_2$SO$_4$, which is agitated. When the pH is 3.8, the addition of sodium silicate is stopped and the resulting sol, together with 2 drops of a sodium alkyl sulfonate, are poured into 8 l of vigorously agitated trichloroethylene. The hydrogel balls formed precipitate. 1 l of ammoniated water pH 9 is added, followed by filtration.

The balls are washed 3 times with N/10 HCl, then with water. The hydrogel produced contains 80% of water.

120 g of the hydrogel, 15 g of triethoxy-iodopropylsilane and 200 ml of benzene are then heated at boiling temperature. In 3 hours, 95 ml of water is separated by azeotropic distillation.

After cooling, the product formed is drained, washed with acetone and dried.

The result is a silica grafted by iodopropylsilane groups, containing 2.1% by weight of iodine, whose grain size is less than 200 μ, specific surface area is 425 sq. m/g and pore volume is 1.1 ml/g.

Modification of the grafted silica:

11 g of the grafted silica is introduced into 25 ml of a benzene solution containing 1.5 g of the compound $H_2N - (CH_2)_3 - NH-(CH_2)_2-C_6H_4$ COO C$_2$H$_5$ and the dispersion is heated under reflux for 24 hours.

After cooling, the silica is filtered and washed with ethanol at 95°C to dissolve any unreacted compound. This compound being colored, the washing operation is continued until the solvent is colorless. The silica is then washed with water.

The resulting product and 50 ml of 4 N HCl are then heated at boiling temperature for 24 hours, in order to convert the ester function into an acid function.

After cooling, the balls are filtered and washed with distilled water, and then the PH is balanced at 8.6 with a pyrophosphate buffer solution.

The amount of compound fixed is approximately 1 g.

Purification of the d-aminoacid oxidase:

11 G of the modified grafted silica produced is introduced into a column for chromatography, then 5 ml of a pH 8.5 pyrophosphate buffer solution, containing 150 mg of the mixture of proteins to be treated, comprising d-aminoacid oxidase to be purified and inactive proteins, are circulated at a speed of 9 ml/h.

Enzymatic activity is determined on the solution issuing from the column, by the addition of d-alanine in 0.2 M pH 8.3 pyrophosphate buffer, then dinitrophenylhydrazine, and the absorbence is measured at 440 nm. The solution has no enzymatic activity, which shows that the d-aminoacid oxidase has been retained on the carrier.

Water is then circulated in the column, at the same speed, until metering by spectrometry at 280 nm, carried out on the solution issuing from the column, confirms that there is no longer any inactive protein absorbed on the carrier.

The inactive proteins represent 90% of all of the proteins introduced.

20 ml of a pH 8.5 pyrophosphate buffer solution, containing 30% by volume of ethyleneglycol, is then introduced into the column at a rate of 9 ml/h.

Enzymatic activity is measured in the solution issuing from the column, as described above. The activity represents 90% of the activity of the initial mixture. The enrichment factor is approximately 100.

We claim:

1. A process for the separation and purification of d-aminoacid oxidase, which comprises contacting a solution of a mixture of proteins containing the d-aminoacid oxidase with a carrier onto which the enzyme is fixed, then separating the d-aminoacid oxidase from the carrier, characterized in that the carrier is a mineral carrier bearing haloalkylsilane grafts modified by fixing residues having the formula $-NH-(CH_2)_3-NH-(CH_2)_2C_6H_4\ COOH$, and that the purified d-aminoacid oxidase is separated from the carrier by dissolution in a solution of ethyleneglycol.

2. A process according to claim 1, characterized in that the grafted carrier is an oxide, hydroxide or other porous insoluble mineral compound upon which are grafted, substituted or unsubstituted, haloalkylsilane groups whose alkyl residue comprises from 3 to 11 carbon atoms.

3. A process according to claim 2, characterized in that the grafted carrier is modified by reacting the grafted carrier with the compound having the formula

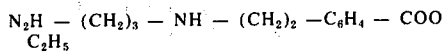

then treating the resulting product with a concentrated acid.

4. A process according to claim 1, characterized in that the concentration of the ethyleneglycol solution is less than 50% by volume.

* * * * *